United States Patent [19]

Bright

[11] Patent Number: 4,727,178
[45] Date of Patent: Feb. 23, 1988

[54] PROCESS FOR PREPARING PHOSPHORODICHLORIDOTHIOLATE

[75] Inventor: Danielle A. Bright, Brooklyn, N.Y.

[73] Assignee: Stauffer Chemical Co., Westport, Conn.

[21] Appl. No.: 885,492

[22] Filed: Jul. 14, 1986

[51] Int. Cl.$^4$ ................................................ C07F 9/20
[52] U.S. Cl. ...................................... 558/097; 558/95
[58] Field of Search .................................. 558/95–97, 558/202

[56] References Cited

U.S. PATENT DOCUMENTS 4,056,581 11/1977 Bayer et al. .......................... 558/202

Primary Examiner—Anton H. Sutto
Attorney, Agent, or Firm—Vivienne T. White; Michael J. Bradley

[57] ABSTRACT

S-substituted phosphorodichloridothiolates such as S-alkyl, cycloalkyl, aralkyl, and arylphosphorodichloridothiolates are prepared by reacting a sulfuryl chloride and a mercaptan or disulfide with phosphorus trichloride and a carboxylic acid anhydride.

15 Claims, No Drawings

PROCESS FOR PREPARING PHOSPHORODICHLORIDOTHIOLATE

DETAILED DESCRIPTION OF THE RELATED ART

The invention relates to a process for preparing S-substituted phosphorodichloridothiolates and particularly S-alkyl, cycloalkyl, aralkyl, and aryl phosphorodichloridothiolates.

A process for preparing such compounds is disclosed in U.S. Pat. No. 4,056,581. The process disclosed therein is the reaction of an alkyl, cycloalkyl, aralkyl or aryl sulfenyl chloride, which can be formed in situ, with phosphorus trichloride and a carboxylic acid or water to form the corresponding phosphorodichloridothiolates in high yields and purity.

The compounds produced by the process of this invention are useful as intermediates in the preparation of certain O,S-disubstituted phosphorochloridothiolates, which in turn are useful as intermediates in the preparation of known organophosphorus pesticides, such as those described in U.S. Pat. Nos. 3,374,293, 3,784,654, and 3,839,509. The phosphorodichloridothiolates of the present invention can be converted to O,S-disubstituted phosphorochloridothiolates by various methods readily available to those skilled in the art. One method involves reaction of the S-substituted phosphorodichloridothiolate with an alcohol in the presence of an acid scavenger, e.g., a tertiary amine, to produce the corresponding O,S-disubstituted phosphorochloridothiolate.

SUMMARY OF THE INVENTION

The invention is directed to the preparation of certain S-substituted phosphorodichloridothiolates by reacting an alkyl, cycloalkyl, aralkyl or aryl sulfenyl chloride, which can be prepared in situ, with phosphorus trichloride and a carboxylic acid anhydride to form the corresponding alkyl, cycloalkyl, aralkyl, or aryl phosphorodichloridothiolate.

DETAILED DESCRIPTION OF THE INVENTION

The invention comprises the preparation of S-substituted phosphorodichloridothiolates by reacting a chlorinating agent with a second reactant which can be a mercaptan of the formula RSH or disulfide of the formula RSSR, wherein R is an alkyl, aralkyl or substituted cycloalkyl or aryl or substituted aryl with a phosphorus trichloride and a carboxylic acid anhydride.

The process also comprises preparing S-substituted phosphorodichloridothiolates by reacting a sulfenyl chloride with phosphorus trichloride and a carboxylic acid anhydride.

The invention, in a preferred embodiment, is directed to the production of compounds such as those having the formula:

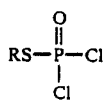  (1)

wherein R is
(a) a $(C_1-C_{10})$ alkyl, preferably a $(C_1-C_7)$ alkyl, most preferably a $(C_1-C_4)$ alkyl group, optionally substituted with a $(C_1-C_4)$ alkoxy group, preferably a methoxy or ethoxy group; a $(C_1-C_4)$ alkylthio group, preferably a methylthio or ethylthio group; or a halogen atom, preferably a chlorine atom;

(b) a $(C_3-C_4)$ cycloalkyl group, preferably a cyclohexyl group;

(c) a $(C_7-C_{10})$ aralkyl, preferably benzyl or phenethyl group, optionally substituted with up to three $(C_1-C_2)$ alkyl groups, preferably methyl groups; $(C_1-C_2)$ alkoxy groups, preferably methoxy groups; halogen atoms, preferably chlorine atoms; or nitro groups; or (d) a $(C_4-C_{10})$ aryl, preferably phenyl group, optionally substituted with up to three $(C_1-C_5)$ alkyl groups, preferably methyl groups; $(C_1-C_5)$ alkoxy groups, preferably methoxy groups; halogen atoms, preferably chlorine atoms; or nitro groups.

In a preferred embodiment of this invention, R is a $(C_1-C_7)$ alkyl group, especially a $(C_2-C_4)$ alkyl group.

As used in the specification and claims, the terms alkyl, alkoxy, alkylthio, and aralkyl refer to groups having a straight or branched chain spatial configuration.

The process of the present invention involves reacting a mercaptan or a disulfide of the formulas:

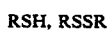

respectively, wherein R is as previously stated above with a chlorinating agent and phosphorus trichloride in the presence of a carboxylic acid anhydride to produce the above reaction product (1) wherein sulfenyl chloride is formed in situ. Suitable disulfides for use in practicing the invention can comprise the following: methyl disulfide, ethyl disulfide, n-propyl disulfide, isopropyl disulfide, n-butyl disulfide, isobutyl disulfide, sec-butyl disulfide, n-amyl disulfide, n-hexyl disulfide, n-decyl disulfide, 2-(n-propoxyethyl) disulfide, 2-methylthio-n-propyl disulfide, 2-chloroethyl disulfide, cyclohexyl disulfide, benzyl disulfide, 2-chlorophenethyl disulfide, phenyl disulfide, bis-2-methylphenyl disulfide, bis-4-ethylphenyl disulfide, bis-3,5-dimethyl-4-methoxyphenyl disulfide, bis-4-ethoxyphenyl disulfide, bis-3-bromophenyl disulfide, bis-4-chlorophenyl disulfide, bis-2,5-dichlorophenyl disulfide, bis-2,4,6-trichlorophenyl disulfide, bis-2,4-dichloro-6-methylphenyl disulfide, bis-2-chloro-4-propoxyphenyl disulfide, bis-2-chloro-4-bromophenyl disulfide, bis-4-fluorophenyl disulfide, bis-4-nitrophenyl disulfide, bis-2-nitro-4-chlorophenyl disulfide, bis-2-nitro-4-methylphenyl disulfide, bis-naphthyl disulfide, bis-3,5-dimethylnaphthyl disulfide, bis-3-chloronaphthyl disulfide, and the like.

The mercaptans can comprise: methyl mercaptan, ethyl mercaptan, n-propyl mercaptan, isopropyl mercaptan, n-butyl mercaptan, isobutyl mercaptan, sec-butyl mercaptan, n-amyl mercaptan, n-hexyl mercaptan, n-decyl mercaptan, 2-(n-propoxyethyl) mercaptan, 2-methylthio-n-propyl mercaptan, 2-chloroethyl mercaptan, cyclohexyl mercaptan, benzyl mercaptan, 2-chlorophenethyl mercaptan, thiophenol, 2-methyl thiophenol, 4-ethyl thiophenol, 3,5-dimethyl-4-methoxy thiophenol, 4-ethoxy thiophenol, 3-bromothiophenol, 4-chlorothiophenol, 2,5-dichloro thiophenol, 2,4,6-thrichloro thiophenol, 2,4-dichloro-6-methyl thiophenol, 2-chloro-4-propoxy thiophenol, 2-chloro-4-bromo thiophenol, 4-fluoro thiophenol, 4-nitro thiophenol, 2-nitro-4-chloro-thiophenol, 2-nitro-4-methyl thiophenol, naphthyl mercaptan, 3,5-dimethylnaphthyl mercaptan, 3-chloronaphthyl mercaptan, and the like.

The invention can also contemplate utilizing a sulfenyl chloride of the formula:

R—S—Cl wherein R is as defined for formula (1) with phosphorus trichloride and a carboxylic acid anhydride. The sulfenyl chloride can be formed in situ by the reaction of the mercaptan as a disulfide with a chlorinating agent such as chloride or sulfuryl chloride.

Any carboxylic acid anhydride can be employed in the process of this invention; however a non-keto, non-aldo containing carboxylic acid anhydride is preferred, i.e., an acid other than a ketocarboxylic acid anhydride or aldocarboxylic acid anhydride is preferred.

The more preferred carboxylic acid anhydride can be represented by the formula:

$$Y-\overset{O}{\underset{\parallel}{C}}-O-\overset{O}{\underset{\parallel}{C}}-R_1$$

wherein Y and $R_1$ are the same or different and are a hydrogen atom; a ($C_1$-$C_2$) alkyl group optionally substituted with up to three halogen atoms, preferably chlorine atoms; or a group of the formula:

X—(CH$_2$)$_n$— wherein X is a cyano group; a phenyl group optionally substituted with up to three ($C_1$-$C_5$) alkyl groups, preferably methyl groups, ($C_1$-$C_5$) alkoxy groups, preferably methoxy groups, halogen atoms, preferably chlorine atoms, or nitro groups; or a group of the formula:

$$-\overset{O}{\underset{\parallel}{C}}-R'$$

wherein R' is a hydroxy group; a ($C_1$-$C_5$) alkoxy group; or a phenoxy group, optionally substituted with up to three ($C_1$-$C_5$) alkyl groups, preferably methyl groups, ($C_1$-$C_5$) alkoxy groups, preferably methoxy groups, halogen atoms, preferably chlorine atoms, or nitro groups; and n is an integer from 0 to 8.

The most preferred carboxylic acid anhydride can be represented by the formula:

$$X'-\overset{O}{\underset{\parallel}{C}}-O-\overset{O}{\underset{\parallel}{C}}-R''$$

wherein X' and R'' are the same or different and are a ($C_1$-$C_4$) alkyl group, preferably a ($C_1$-$C_3$) alkyl group, or a phenyl group. Among the most preferred anhydride, acetic anhydride and propionic anhydride are more preferred, acetic anhydride being especially preferred.

The preparative process can be carried out neat or with a solvent; however, the presence of an inert organic solvent is preferred. Suitable solvents include aromatic hydrocarbons such as benzene, toluene, and xylene; aromatic and aliphatic halogenated, especially chlorinated, hydrocarbons such as chlorobenzene, chloroform, carbon tetrachloride, and perchloroethylene; carboxylic acid esters such as ethyl acetate and butyl acetate; and the like. The preferred solvents are aromatic hydrocarbons and halogenated aromatic hydrocarbons, especially toluene, xylene, and chlorobenzene. The most preferred solvent is chlorobenzene.

The reaction is normally conducted at a temperature range of about −20° C. to about 50° C. and preferably at about −5° C. to about 30° C. Generally, a substantially equimolar ratio of reactants is preferred, though up to 100% molar excesses of any of the reactants can be employed.

The reaction products are obtained by fractional distillation at reduced pressures or by other conventional techniques. The products thus obtained can be used in additional syntheses without further purification.

When a mercaptan or disulfide is employed in the formation of the sulfenyl chloride, the reactants can be combined in any order, provided that the chlorinating agent is added to the mercaptan before the phosphorus trichloride. A preferred sequence involves (a) combining the mercaptan or disulfide and the carboxylic acid anhydride, (b) adding the chlorinating agent, and then (c) adding the phosphorus trichloride. A more preferred sequence, split-addition, involves (a) adding a portion, generally about half, of the chlorinating agent to the mercaptan or disulfide, (b) adding the carboxylic acid anhydride, (c) adding the phosphorus trichloride, and (d) adding the remainder of the chlorinating agent.

Reaction conditions such as choice of solvents and temperature correspond to the conditions described above. Although stoichiometric quantities of the reactants are generally sufficient for carrying out the reaction, up to 100% molar excesses of any of the reagents can be employed. The preferred molar ratio is 1 mole of mercaptan to 1.1 moles of chlorinating agent to 1 mole of anhydride to 1 mole of PCl$_3$.

Suitable chlorinating agents include chlorine, sulfuryl chloride, N-chlorosuccinimide and the like. Chlorine and sulfuryl chloride are more preferred, chlorine being most preferred.

The reaction products can be obtained by fractional distillation at reduced pressures or by other conventional techniques. The products obtained can be used in additional syntheses without further purification.

EXAMPLE 1

Synthesis of O-Ethyl-S-propylphosphorochloridothiolate was as follows:

$$CH_3CH_2CH_2SH + SO_2Cl_2 + PCl_3 + (CH_3\overset{O}{\underset{\parallel}{C}})_2-O \longrightarrow$$

$$CH_3CH_2CH_2S-\overset{O}{\underset{\parallel}{P}}-Cl_2 + 2CH_3COCl + SO_2 + HCl$$

To a solution containing 27.1 ml of propyl mercaptan (0.3 mole, 22.8 g) in 60 ml of toluene cooled to between −5° C. and 0° C. was added 12.0 ml of SO$_2$Cl$_2$ (0.15 mole, 20.2 g). The temperature was not allowed to rise above 0° C. A 0.3 molar (30.6 g, 28.3 ml) amount of acetic anyydride was quickly added, followed by 0.3 mole (41.2 g, 26.2 ml) of PCl$_3$. The intense temperature was maintained between −5° C. and 0° C. A 14.3 ml amount of SO$_2$Cl$_2$ (0.18 mole, 24.0 g) was added with the temperature at −5° C. to 0° C. The reaction mixture was stirred at room temperature for 2 hours. Acetyl chloride and toluene were removed under vacuum (water aspirator). The remaining product distilled. The yield of the product was 57.4 grams corresponding to an 84% yield.

EXAMPLE 2

In the preparation of S-propylphosphorodichloridothiolate according to another embodiment of the invention, a solution of 0.3 mole of propyl mercaptan (22.8 g, 27.1 ml) in 60 ml toluene, cooled to −5° C., was treated dropwise with 0.33 mole of sulfuryl chloride (44.2 g, 26.4 ml) over a period of 30 minutes. The temperature was not allowed to rise above 0° C. during the addition. 0.3 mole (30.6 g, 28.3 ml) of acetic anhydride was added at 0° C., followed by 0.3 mole of $PCl_3$ (41.2 g, 26.2 ml) also at 0° C. The reaction mixture was stirred at room temperature for 2 hours. Acetyl chloride and toluene were distilled under vacuum (water aspirator). Distillation in vacuo of the residue gave 45.3 g of S-propylphosphorodichloridothiolate (78% yield, b.p. 94°–97° [5 mm]).

What is claimed is:

1. A process for preparing S-substituted phosphorodichloridothiolate of the formula:

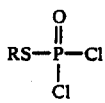

wherein R is
(a) a ($C_1$–$C_{10}$) alkyl, preferably a ($C_1$–$C_7$) alkyl, most preferably a ($C_1$–$C_4$) alkyl group, optionally substituted with a ($C_1$–$C_4$) alkoxy group, preferably a methoxy or ethoxy group; a ($C_1$–$C_4$) alkylthio group, preferably a methylthio or ethylthio group; or a halogen atom, preferably a chlorine atom;
(b) a ($C_3$–$C_4$) cycloalkyl group, preferably a cyclohexyl group;
(c) a ($C_7$–$C_{10}$) aralkyl, preferably benzyl or phenethyl group, optionally substituted with up to three ($C_1$–$C_2$) alkyl groups, preferably methyl groups; ($C_1$–$C_2$) alkoxy groups, preferably methoxy groups; halogen atoms, preferably chlorine atoms; or nitro groups; or
(d) a ($C_4$–$C_{10}$) aryl, preferably phenyl group, optionally substituted with up to three ($C_1$–$C_5$) alkyl groups, preferably methyl groups; ($C_1$–$C_5$) alkoxy groups, preferably methoxy groups; halogen atoms, preferably chlorine atoms; or nitro groups, which comprises reacting a chlorinating agent with a second reactant selected from a mercaptan of the formula RSH and a disulfide of the formula RSSR, wherein R is as previously stated, and with phosphorus trichloride and carboxylic acid anhydride at a temperature sufficient to produce the phosphorodichloridothiolate product.

2. A process for preparing S-substituted phosphorodichloridothiolates comprising recting a sulfenyl chloride with phosphorus trichloride and a carboxylic acid anhydride.

3. A process for preparing S-substituted phosphorodichloridothiolates comprising reacting a chlorinating agent and a second reactant selected from a mercaptan of the formula RSH and a disulfide of the formula RSSR, wherein R is an alkyl, aralkyl or substituted cycloalkyl or aryl or substituted aryl, with a phosphorus trichloride and a carboxylic acid anhydride.

4. The process of claim 3 wherein the chlorinating agent is sulfuryl chloride.

5. The process of claim 3 wherein the temperature range for the process is from about −20° C. to about 50° C.

6. The process of claim 5 wherein the temperature range for the process is from about −5° C. to about 30° C.

7. The process of claim 3 wherein the reaction is carried out in the presence of an inert organic solvent.

8. The process of claim 6 wherein the solvent is an aromatic hydrocarbon, an aromatic or aliphatic halogenated hydrocarbon or a carboxylic acid ester.

9. The process of claim 3 wherein the carboxylic acid anhydride has the formula:

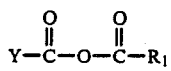

and wherein Y and $R_1$ are the same or different and are a hydrogen atom; a ($C_1$–$C_2$) alkyl group optionally substituted with up to three halogen atoms, preferably chlorine atoms; or a group of the formula:

wherein X is a cyano group; a phenyl group optionally substituted with up to three ($C_1$–$C_5$) alkyl groups, preferably methyl groups, ($C_1$–$C_5$) alkoxy groups, preferably methoxy groups, halogen atoms, preferably chlorine atoms, or nitro groups; or a group of the formula:

wherein R' is a hydroxy group; a ($C_1$–$C_5$) alkoxy group; or a phenoxy group, optionally substituted with up to three ($C_1$–$C_5$) alkyl groups, preferably methyl groups, ($C_1$–$C_5$) alkoxy groups, preferably methoxy groups, halogen atoms, preferably chlorine atoms, or nitro groups; and n is an integer from 0 to 8.

10. The process of claim 9 wherein the carboxylic acid anhydride is

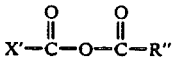

wherein X' and R'' are the same or different and are a ($C_1$–$C_4$) alkyl group, preferably a ($C_1$–$C_3$) alkyl group, or a phenyl group.

11. The process of claim 9 wherein the carboxylic acid anhydride is acetic anhydride.

12. The process of claim 2 wherein a sulfenyl chloride of the formula:

wherein R is
(a) a ($C_1$–$C_{10}$) alkyl, preferably a ($C_1$–$C_7$) alkyl, most preferably a ($C_1$–$C_4$) alkyl group, optionally substituted with a ($C_1$–$C_4$) alkoxy group, preferably a methoxy or ethoxy group; a ($C_1$–$C_4$) alkylthio group, preferably a methylthio or ethylthio group; or a halogen atom, preferably a chlorine atom;
(b) a ($C_3$–$C_4$) cycloalkyl group, preferably a cyclohexyl group;

(c) a ($C_7$–$C_{10}$) aralkyl, preferably benzyl or phenethyl group, optionally substituted with up to three ($C_1$–$C_2$) alkyl groups, preferably methyl groups; ($C_1$–$C_2$) alkoxy groups, preferably methoxy groups; halogen atoms, preferably chlorine atoms; or nitro groups; or (d) a ($C_4$–$C_{10}$) aryl, preferably phenyl group, optionally substituted with up to three ($C_1$–$C_5$) alkyl groups, preferably methyl groups; ($C_1$–$C_5$) alkoxy groups, preferably methoxy groups; halogen atoms, preferably chlorine atoms; or nitro groups, is formed in situ by the reaction of a compound selected from a mercaptan and a disulfide, with a chlorinating agent.

13. The process of claim 1 wherein the chlorinating agent is sulfuryl chloride.

14. The process of claim 1 wherein the chlorinating agent is added in a split addition to the reactions.

15. A process for preparing S-substituted phosphorodichloridothiolate of the formula:

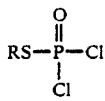

wherein R is
 (a) a ($C_1$–$C_{10}$) alkyl, preferably a ($C_1$–$C_7$) alkyl, most preferably a ($C_1$–$C_4$) alkyl group, optionally substituted with a ($C_1$–$C_4$) alkoxy group, preferably a methoxy or ethoxy group; a ($C_1$–$C_4$) alkylthio group, preferably a methylthio or ethylthio group; or a halogen atom, preferably a chlorine atom;
 (b) a ($C_3$–$C_4$) cycloalkyl group, preferably a cyclohexyl group;
 (c) a ($C_7$–$C_{10}$) aralkyl, preferably benzyl or phenethyl group, optionally substituted with up to three ($C_1$–$C_2$) alkyl groups, preferably methyl groups; ($C_1$–$C_2$) alkoxy groups, preferably methoxy groups; halogen atoms, preferably chlorine atoms; or nitro groups; or
 (d) a ($C_4$–$C_{10}$) aryl, preferably phenyl group, optionally substituted with up to three ($C_1$–$C_5$) alkyl groups, preferably methyl groups; ($C_1$–$C_5$) alkoxy groups, preferably methoxy groups; halogen atoms, preferably chlorine atoms; or nitro groups,
which comprises reacting a sulfenyl chloride with phosphorus trichloride and a carboxylic acid anhydride at a temperature sufficient to produce the phosphorodichloridothiolate product.

* * * * *